(12) United States Patent
Moyes et al.

(10) Patent No.: US 6,479,480 B1
(45) Date of Patent: Nov. 12, 2002

(54) PHENYLINDOLE DERIVATIVES AS 5-HT2A RECEPTOR LIGANDS

(75) Inventors: Christopher Richard Moyes, Sawbridgeworth (GB); Michael Rowley, Chelmsford (GB)

(73) Assignee: Merck Sharp & Dohme Ltd., Hoddesdon (GB)

(*) Notice: Subject to any disclaimer, the term of this patent is extended or adjusted under 35 U.S.C. 154(b) by 0 days.

(21) Appl. No.: 09/743,743

(22) PCT Filed: Jul. 15, 1999

(86) PCT No.: PCT/GB99/02294

§ 371 (c)(1),
(2), (4) Date: Jan. 12, 2001

(87) PCT Pub. No.: WO00/05229

PCT Pub. Date: Feb. 3, 2000

(30) Foreign Application Priority Data

Jul. 24, 1998 (GB) ............................................ 9816263

(51) Int. Cl.[7] .................. C07D 401/06; C07D 403/06; A61K 31/40
(52) U.S. Cl. .............................. 514/217.08; 514/235.2; 514/254.09; 514/299; 514/323; 514/415; 540/602; 544/143; 544/373; 546/112; 546/201; 548/511
(58) Field of Search .......................... 540/602; 544/143, 544/373; 546/112, 201; 548/511; 514/217.08, 235.2, 254.09, 299, 323, 415

(56) References Cited

U.S. PATENT DOCUMENTS 5,703,070 A 12/1997 Lavielle et al. ............ 514/212

FOREIGN PATENT DOCUMENTS

| EP | 0 465 398 A2 | 6/1991 |
|---|---|---|
| EP | 0 747 379 A1 | 6/1996 |
| WO | WO 91/18602 | 12/1991 |

OTHER PUBLICATIONS

R.C. Larock and E.K. Yum, J. Am. Chem. Soc., 113: 6689 (1991).
T. Mano et. al., Investigative Ophthamology and Visual Sciences, 36:S719 (1995).
H. Takenaka et al., Investigative Ophthamology and Visual Sciences, 36: S734 (1995).
D.C. Dyer, Life Sciences, Pharmacology Lett., 53: PL223–PL228 (1995).
Bondarenko et al., Chemical Abstract 91:5093w, 1979.*
Tucker, Psychiatric Disorders in Medical Practice, Cecil Textbook of Medicine, 20th Edition, Vol. 2, pp. 1996–2006, 1996.*

* cited by examiner

Primary Examiner—Deepak R. Rao
(74) Attorney, Agent, or Firm—J. Eric Thies; Shu M. Lee; Melvin Winokur

(57) ABSTRACT

Compounds according to Formula (I) or a salt thereof are selective antagonists of the human 5-HT2A receptor useful for treatment of adverse conditions of the central nervous system:

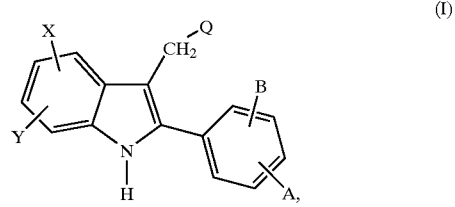

8 Claims, No Drawings

PHENYLINDOLE DERIVATIVES AS 5-HT2A RECEPTOR LIGANDS

CROSS REFERENCE TO RELATED APPLICATIONS

This application is a U.S. National Phase application under 35 U.S.C. §371 of PCT Application No. PCT/GB99/02294, filed Jul. 15, 1999 (published in English), which claims priority under 35 U.S.C. §119 from GB Application No. 9921351.4, filed Sep. 9, 1999.

The present invention relates to a class of indole derivatives which act on serotonin receptors (also known as 5-hydroxytryptamine or 5-HT receptors). More particularly, the invention concerns 1H-indole derivatives bearing an optionally substituted phenyl moiety at the 2-position of the indole ring system and a methylene-linked heterocyclic moiety at the 3-position of the indole ring system. These compounds are selective antagonists of the human 5-HT$_{2A}$ receptor and are therefore useful as pharmaceutical agents, especially in the treatment and/or prevention of adverse conditions of the central nervous system, including psychotic disorders such as schizophrenia.

Schizophrenia is a disorder which is conventionally treated with drugs known as neuroleptics. In many cases, the symptoms of schizophrenia can be treated successfully with so-called "classical" neuroleptic agents such as haloperidol. Classical neuroleptics generally are antagonists at dopamine $D_2$ receptors.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which plainly detract from the clinical desirability of classical neuroleptics, are believed to be attributable to $D_2$ receptor blockade in the striatal region of the brain.

The compound (+)-α-(2,3-dimethoxyphenyl)-1-[2-(4-fluorophenyl)-ethyl]-4-piperidinemethanol (also known as MDL-100,907) is described in WO 91/18602. In preclinical studies, MDL-100,907 failed to induce catalepsy and failed to block apomorphine-induced stereotyped behaviour in animal models, strongly suggesting that this compound would be free from any liability to cause extrapyramidal side-effects. MDL-100,907 is currently undergoing clinical trials in schizophrenic patients and has demonstrated efficacy in a multicentre, placebo-controlled study for antipsychotic potential, with no neurological adverse effects. Pharmacologically, MDL-100,907 has been shown to be a potent antagonist of human 5-HT$_{2A}$ receptors, whilst being essentially devoid of activity at the human dopamine $D_2$ receptor. It is accordingly believed that compounds which can interact selectively with the 5-HT$_{2A}$ receptor relative to the dopamine $D_2$ receptor will display the beneficial level of antipsychotic activity associated with 5-HT$_{2A}$ receptor antagonism, whilst minimizing or even avoiding the extrapyramidal and other side-effects arising from an interaction with dopamine $D_2$ receptors.

SUMMARY OF THE INVENTION

The present invention is described to compounds according to Formula (I) or a salt thereof which are selective antagonist of the human 5-HT$_{2A}$ receptor useful for treatment of adverse conditions of the central nervous system:

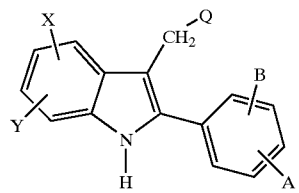

(I)

DETAILED DESCRIPTION OF THE INVENTION

The compounds of the present invention are potent antagonists of the human 5-HT$_{2A}$ receptor, and are accordingly of benefit in the treatment and/or prevention of psychotic disorders such as schizophrenia. The compounds of the invention display more effective binding to the human 5-HT$_{2A}$ receptor than to the human dopamine $D_2$ receptor, and they can therefore be expected to manifest fewer side-effects than compounds which do not discriminate in their binding affinity as between 5-HT$_{2A}$ and $D_2$ receptors.

By virtue of their potent human 5-HT$_{2A}$ receptor antagonist activity, the compounds of the present invention are also effective in the treatment of neurological conditions including depression, anxiety, panic disorder, obsessive-compulsive disorder, pain, sleep disorders such as insomnia, eating disorders such as anorexia nervosa, and dependency or acute toxicity associated with narcotic agents such as LSD or MDMA; and cardiovascular conditions including variant angina, Raynaud's phenomenon, intermittent claudication, coronary and peripheral vasospasms, fibromyalgia, cardiac arrhythmias and thrombotic illness. They may also be generally of benefit in the inhibition of platelet aggregation, as well as in controlling the extrapyramidal symptoms associated with the administration of neuroleptic agents. They may further be effective in the lowering of intraocular pressure and may therefore be beneficial in treating glaucoma (cf. T. Mano et al. and H. Takaneka et al., *Investigatiue Ophthalmology and Visual Science*, 1995, Vol. 36, pages 719 and 734 respectively).

Being 5-HT$_{2A}$ receptor antagonists, the compounds of the present invention may also be beneficial in preventing or reducing the toxic symptoms associated with the intake of ergovaline in animals consuming *Acremonium coenophialum* infected tall fescue (cf. D. C. Dyer, *Life Sciences*, 1993, 53, 223–228).

The compounds according to the present invention are potent and selective 5-HT$_{2A}$ receptor antagonists having a human 5-HT$_{2A}$ receptor binding affinity ($K_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine $D_2$ receptor.

The present invention provides a compound of formula I, or a salt thereof:

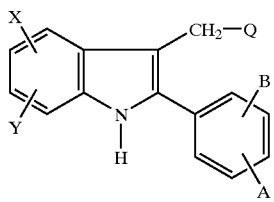

(I)

wherein

- A and B independently represent hydrogen, halogen, cyano, nitro, trifluoromethyl, trifluoromethoxy, $C_{1-6}$ alkyl or $C_{1-6}$ alkoxy;
- X and Y independently represent hydrogen, halogen, trifluoromethyl, trifluoromethoxy, $C_{1-6}$ alkyl, $C_{1-6}$ alkoxy or phenyl; and
- Q represents a substituted five-, six- or seven-membered monocyclic heteroaliphatic ring containing one nitrogen atom and optionally one other heteroatom selected from oxygen, sulphur and nitrogen; or Q represents a substituted 6- to 11-membered bicyclic heteroaliphatic ring system which contains one nitrogen atom as the sole heteroatom; the moiety Q being linked to the remainder of the molecule via a carbon atom.

When Q represents a monocyclic heteroaliphatic ring, this is suitably a substituted pyrrolidine, piperidine, hexamethyleneimine, morpholine, thiomorpholine or piperazine ring linked through a carbon atom to the remainder of the molecule of formula I as depicted above.

When Q represents a bicyclic heteroaliphatic ring system, this is suitably a substituted 2-azabicyclo[2.2.2]octane or 2-azabicyclo[2.2.1]heptane ring system linked through a carbon atom to the remainder of the molecule of formula I as depicted above.

The moiety Q may typically be substituted by one, two or three substituents, suitably by one or two substituents. Preferably, the moiety Q is substituted, as appropriate, by the substituents $R^1$, $R^2$ and $R^3$ as defined below.

Typical values for the moiety Q include the structures of formula Qa to Qm:

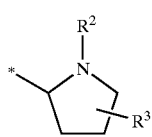

(Qa)

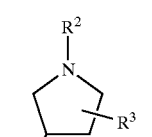

(Qb)

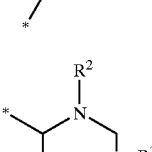

(Qc)

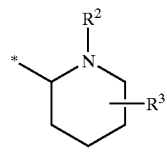

(Qd)

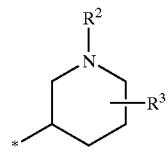

(Qe)

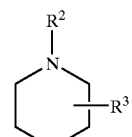

(Qf)

(Qg)

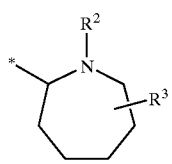

(Qh)

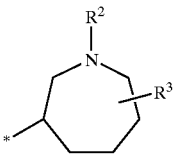

(Qj)

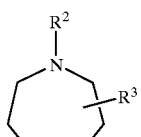

(Qk)

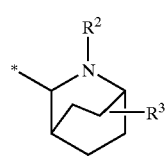

(Qm)

in which the asterisk denotes the point of attachment to the remainder of the molecule;

Z represents oxygen, sulphur or N—$R^1$;

$R^1$ and $R^2$ independently represent hydrogen; or $C_{1-6}$ alkyl, aryl($C_{1-6}$)alkyl or $C_{3-7}$ heterocycloalkyl($C_{1-6}$) alkyl, any of which groups may be optionally substituted by one or more substituents; and $R^3$ represents hydrogen, halogen, $C_{1-6}$ alkyl, hydroxy or $C_{1-6}$ alkoxy; provided that at least one of $R^1$, $R^2$ and $R^3$ is other than hydrogen.

Particular values for the moiety Q include the structures of formula Qa, Qb, Qc, Qd, Qe, Qg, Qk and Qm above.

Where it is other than hydrogen, the group $R^2$ may be optionally substituted by one or more substituents. Suitably, the group $R^2$ is unsubstituted, or substituted by one or two substituents. In general, the group $R^2$ may be unsubstituted or monosubstituted. Examples of optional substituents on the group $R^2$ include halogen, cyano, trifluoromethyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$)alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, aminosulphonylmethyl, $C_{1-6}$ alkylaminosulphonylmethyl and di($C_{1-6}$)alkylaminosulphonylmethyl.

A particular substituent on the group $R^2$ is methoxy.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

Typical aryl groups include phenyl and naphthyl, preferably phenyl.

The expression "aryl($C_{1-6}$)alkyl" as used herein includes benzyl, phenylethyl, phenylpropyl and naphthylmethyl, especially phenylethyl.

Typical heterocycloalkyl groups include azetidinyl, pyrrolidinyl, piperidinyl, piperazinyl, morpholinyl, thiomorpholinyl and imidazolidinonyl groups.

A particular $C_{3-7}$ heterocycloalkyl($C_{1-6}$)alkyl group is imidazolidinonylethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Particular values for the substituent A in the compounds of formula I above include hydrogen, fluoro, trifluoromethyl, methyl and methoxy, especially hydrogen or fluoro.

Suitably, B represents hydrogen, fluoro, chloro, cyano, nitro, trifluoromethyl, trifluoromethoxy, methyl or methoxy, especially hydrogen.

Particular values for the substituent X include hydrogen, fluoro and methoxy, especially hydrogen.

Suitably, Y represents hydrogen, fluoro, chloro, bromo, methyl, methoxy or phenyl, especially hydrogen, fluoro or chloro. In one embodiment, Y represents hydrogen or fluoro.

Suitably, the moiety Q represents a group of formula Qc as depicted above.

Suitably, Z represents oxygen or N—$R^1$, especially N—$R^1$.

Suitably, $R^1$ represents hydrogen or $C_{1-6}$ alkyl, especially hydrogen or methyl. In one embodiment, $R^1$ represents methyl. In another embodiment, $R^1$ represents hydrogen.

Suitable values of $R^2$ include hydrogen, methyl, ethyl, methoxyethyl, benzyl, phenylethyl and phenylpropyl. In one embodiment, $R^2$ represents hydrogen. In another embodiment, $R^2$ represents methyl.

Suitably, $R^3$ represents hydrogen, halogen or $C_{1-6}$ alkyl. Particular values of $R^3$ include hydrogen, fluoro and methyl, typically hydrogen or methyl, and especially hydrogen.

A particular sub-class of compounds according to the invention is represented by the compounds of formula II, and salts thereof:

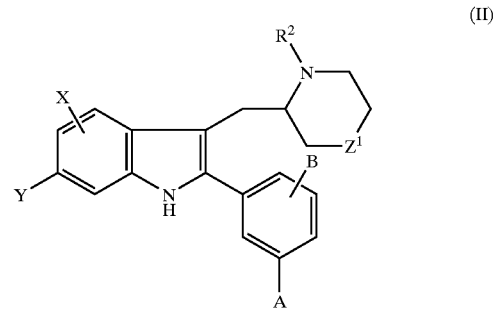

(II)

wherein
$Z^1$ represents oxygen, N—$R^1$ or CH—$R^3$; and
A, B, X, Y, $R^1$, $R^2$ and $R^3$ are as defined with reference to formula I above.

Suitably, $Z^1$ represents oxygen or N—$R^1$.

Preferably, $Z^1$ represents N—$R^1$.

Specific compounds within the scope of the present invention include:

3-(1-methylpiperidin-3-ylmethyl)-2-phenyl-1H-indole;
3-(1-methylpyrrolidin-3-ylmethyl)-2-phenyl-1H-indole;
3-(1-methylpyrrolidin-2(R)-ylmethyl)-2-phenyl-1H-indole;
3-(1-methylpyrrolidin-2(S)-ylmethyl)-2-phenyl-1H-indole;
2-methyl-3-(2-phenyl-1H-indol-3-ylmethyl)-2-azabicyclo[2.2.2]octane;
3-(2-methyl-2-azabicyclo[2.2.1]hept-3-ylmethyl)-2-phenyl-1H-indole;
3-(1,5-dimethyl-cis-pyrrolidin-2-ylmethyl)-2-phenyl-1H-indole;
3-(1,4-dimethylpiperazin-2(S)-ylmethyl)-2-phenyl-1H-indole;
7-chloro-3-(1,4-dimethylpiperazin-2(S)-ylmethyl)-2-phenyl-1H-indole;
3-(4-methylmorpholin-3-ylmethyl)-2-phenyl-1H-indole;
3-[1-(2-phenylethyl)piperidin-3-ylmethyl]-2-phenyl-1H-indole;
3-(1-benzylpyrrolidin-2-ylmethyl)-2-phenyl-1H-indole;

3-[1-(2-phenylethyl)pyrrolidin-2-ylmethyl]-2-phenyl-1H-indole;
2-phenyl-3-[1-(3-phenylpropyl)pyrrolidin-2(R)-ylmethyl]-1H-indole;
3-(1-benzylpyrrolidin-3-ylmethyl)-2-phenyl-1H-indole;
3-[1-(2-phenylethyl)pyrrolidin-3-ylmethyl]-2-phenyl-1H-indole;
3-(1-methylpiperidin-2(R)-ylmethyl)-2-phenyl-1H-indole;
3-(1-methylpiperidin-2(S)-ylmethyl)-2-phenyl-1H-indole;
3-(1-methylazepin-2(R)-ylmethyl)-2-phenyl-1H-indole;
3-(1-methylazepin-2(S)-ylmethyl)-2-phenyl-1H-indole;
3-(1-ethylpiperidin-2-ylmethyl)-2-phenyl-1H-indole;
3-[1-(2-methoxyethyl)piperidin-2-ylmethyl]-2-phenyl-1H-indole;
3-(1-benzylpiperidin-2-ylmethyl)-2-phenyl-1H-indole;
3-[1-(2-phenylethyl)piperidin-2-ylmethyl]-2-phenyl-1H-indole ;
2-(3-fluorophenyl)-6-fluoro-3-(4-methylpiperazin-2(S)-ylmethyl)-1H-indole;
2-(3-fluorophenyl)-6-fluoro-3-(1-methylpiperazin-2(S)-ylmethyl)-1H-indole; and salts thereof.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds according to this invention may be co-administered with another anti-schizophrenic medicament, for example one producing its effects via dopamine $D_2$ and/or $D_4$ receptor subtype blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

The compounds according to the present invention wherein the moiety Q is substituted on the or each ring nitrogen atom may be prepared by a process which comprises attachment of the requisite substituent (e.g. the group of formula $R^2$ as defined above) to a precursor compound of formula III:

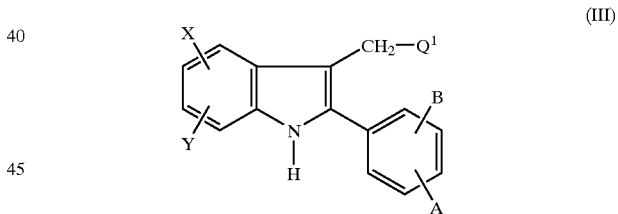

(III)

wherein A, B, X and Y are as defined above, and $Q^1$ corresponds to a moiety of formula Q as defined above in which the or each ring nitrogen atom is unsubstituted; by conventional means including N-alkylation.

Where, for example, the moiety Q represents a structure of formula Qa to Qm as depicted above, attachment of the $R^2$ moiety may conveniently be effected by standard alkylation techniques. One example thereof comprises treatment with an alkyl halide such as methyl iodide or ethyl bromide, an aryl($C_{1-6}$)alkyl halide such as benzyl bromide or 2-phenylethyl bromide, or a $C_{3-7}$ heterocycloalkyl($C_{1-6}$) alkyl halide such as 2-(imidazolidin-2-on-1-yl)ethyl chloride, typically under basic conditions, e.g. potassium carbonate or caesium carbonate in isopropyl alcohol or N,N-dimethylformamide, optionally in the presence of sodium iodide. Another example comprises treatment with an aryl($C_{1-6}$)alkyl mesylate such as 2-phenylethyl methanesulphonate, typically in the presence of sodium carbonate and sodium iodide, in a suitable solvent such as 1,2-dimethoxyethane.

Alternatively, the $R^2$ moiety may conveniently be attached by reductive alkylation, which may be accomplished in a single step, or as a two-step procedure. The single-step approach suitably comprises treating the required precursor compound with the appropriate aldehyde, e.g. formaldehyde, benzaldehyde or phenylacetaldehyde, in the presence of a reducing agent such as sodium cyanoborohydride. In a typical two-step procedure, for the preparation of a product wherein $R^2$ corresponds to a group of formula —$CH_2R^{2a}$, a carboxylic acid derivative of formula $R^{2a}$—$CO_2H$ is condensed with the required precursor compound, suitably in the presence of 1-(3-dimethylaminopropyl)-3-ethylcarbodiimide hydrochloride and 1-hydroxybenzotriazole hydrate, to afford a product wherein $R^2$ represents —$COR^{2a}$; the carbonyl group thereof can then be reduced, for example by treatment with diisobutylaluminium hydride, and the desired product thereby obtained.

The compounds of formula III above may in turn be prepared by reduction of a compound of formula IV:

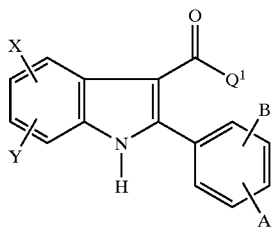

(IV)

wherein A, B, X, Y and $Q^1$ are as defined above.

Similarly, the compounds according to the invention may be prepared by a process which comprises reducing a compound of formula V:

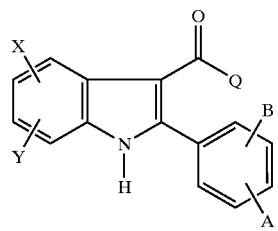

(V)

wherein A, B, X, Y and Q are as defined above.

Moreover, certain compounds according to the invention, in which the moiety Q is substituted on the or each ring nitrogen atom by a methyl group, may be prepared by a process which comprises reducing a compound of formula VI:

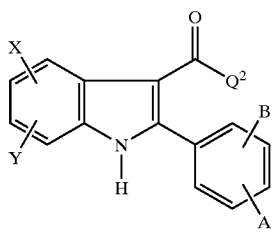

(VI)

wherein A, B, X and Y are as defined above, and $Q^2$ corresponds to a moiety of formula Q as defined above in which the or each ring nitrogen atom is substituted by a benzyloxycarbonyl group.

Reduction of the compounds of formula IV, V and VI above is conveniently accomplished by treatment with a reducing agent such as lithium aluminium hydride, typically at an elevated temperature in an inert solvent, e.g. tetrahydrofuran.

The intermediates of formula IV above may be prepared from the appropriate precursor compound of formula VII:

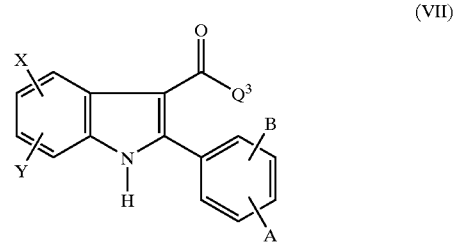

(VII)

wherein A, B, X and Y are as defined above, and $Q^3$ corresponds to a moiety of formula Q as defined above in which the or each ring nitrogen atom is substituted by an amino-protecting group $R^P$; by removal of the or each amino-protecting group $R^P$.

The amino-protecting group $R^P$ referred to above is suitably benzyl, or a carbamoyl moiety such as benzyloxycarbonyl, either of which groups can conveniently be removed as necessary under transfer hydrogenation conditions utilising a hydrogenation catalyst such as palladium on charcoal in the presence of a hydrogen donor such as ammonium formate and/or 1,4-cyclohexadiene, typically in a lower alkanol solvent such as methanol or ethanol.

The intermediates of formula IV to VII above may be prepared by reaction of the appropriate compound of formula Q—COCl, $Q^1$—COCl, $Q^2$—COCl or $Q^3$—COCl with two equivalents of a compound of formula VIII:

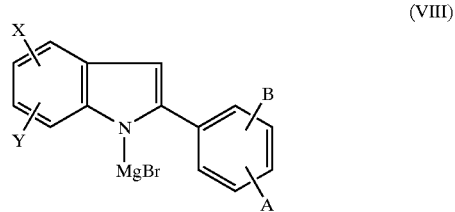

(VIII)

wherein A, B, X, Y, Q, $Q^1$, $Q^2$ and $Q^3$ are as defined above.

The intermediates of formula VIII above are suitably prepared by reacting a compound of formula IX:

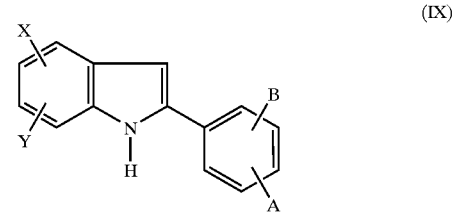

(IX)

wherein A, B, X and Y are as defined above; with a Grignard reagent such as ethyl magnesium bromide.

In another procedure, the compounds according to the invention may be prepared by a process which comprises reacting a compound of formula X or an acid addition salt thereof, typically the hydrochloride salt, with a compound of formula XI:

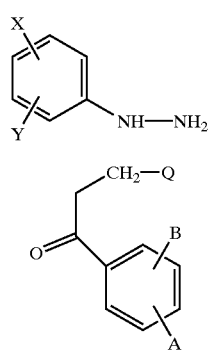

wherein A, B, X, Y and Q are as defined above.

The reaction between compounds X and XI, which is an example of the well-known Fischer indole synthesis, is suitably effected by stirring in ethanol at 25° C., followed by heating in trifluoroacetic acid at 70° C.

Where they are not commercially available, the starting materials of formula IX, X and XI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds in accordance with this invention potently inhibit [$^3$H]-ketanserin binding to the human 5-HT$_{2A}$ receptor expressed in clonal cell lines. Moreover, those compounds of the invention which have been tested display a selective affinity for the 5-HT$_{2A}$ receptor relative to the dopamine D$_2$ receptor.

The compounds of the accompanying Examples were all found to possess a K$_i$ value for displacement of [$^3$H]-ketanserin from the human 5-HT$_{2A}$ receptor, when expressed in Chinese hamster ovary (CHO) clonal cell lines, of 100 nM or less.

EXAMPLE 1

3-(1-Methylpiperidin-3-ylmethyl)-2-phenyl-1H-indole hydrogen oxalate

A. 3-(2-Phenyl-1H-indole-3-carbonyl)piperidine-1-carboxylic acid benzyl ester

A solution of 14.8 g (56.3 mmol) of N-benzyloxycarbonylnipecotic acid in anhydrous dichloromethane (100 ml) under an atmosphere of nitrogen was treated with oxalyl chloride (7.4 ml, 84.4 mmol) followed by 2 drops of N,N-dimethylformamide. The reaction mixture was stirred at room temperature for 90 min at which time the dichloromethane was evaporated in vacuo. The residue was dissolved in anhydrous toluene (75 ml) and the resulting solution evaporated in vacuo. The residue was dissolved in anhydrous benzene (50 ml) to give Solution A.

A solution of 21.7 g (113 mmol) of 2-phenylindole in anhydrous benzene (250 ml) under an atmosphere of nitrogen was added using a cannula to a solution of ethylmagnesium bromide (37.5 ml of a 3M solution in diethyl ether, 113 mmol) and the resulting mixture stirred at room temperature for 15 min to give Solution B.

Solution A was added in one portion to rapidly stirred solution B and the resulting mixture stirred at room temperature for 30 min. The reaction was quenched by the addition of saturated ammonium chloride solution (200 ml). The organic layer was separated, dried over MgSO$_4$ and evaporated in vacuo. The residue was purified by flash chromatography (SiO$_2$; 10% EtOAc in hexanes then 20% EtOAc in hexanes) to afford 15.6 g (35.6 mmol; 63%) of 3-(2-phenyl-1H-indole-3-carbonyl)piperidine-1-carboxylic acid benzyl ester as a clear oil. δ$_H$ (360 MHz; CDCl$_3$) 0.91–1.07 (1H, m, aliphatic), 1.50–1.65 (2H, m, aliphatics), 1.88–1.96 (1H, m, aliphatic), 2.58–2.82 (2H, m, aliphatics), 2.86–3.08 (1H, m, aliphatic), 3.92–4.06 (1H, m, aliphatic), 4.08–4.17 (1H, m, aliphatic), 5.05 (2H, d, J 3.8, PhCH$_2$), 7.24–7.52 (13H, m, aromatics), 8.24–8.30 (1H, m, aromatic), 8.75 (1H, br s, NH); m/z (ES+) 439 (M$^+$+H, 100%).

B. 3-(1-Methylpiperidin-3-ylmethyl)-2-phenyl-1H-indole hydrogen oxalate

To a solution of 4 g (9 mmol) of 3-(2-phenyl-1H-indole-3-carbonyl)piperidine-1-carboxylic acid benzyl ester in anhydrous tetrahydrofuran (25 ml) under an atmosphere of nitrogen was added cautiously over 5 min a solution of lithium aluminium hydride (25 ml of a 1M solution in tetrahydrofuran, 25 mmol) at 0° C. The mixture was heated under reflux for 3 hr, after which it was cooled and quenched by careful addition of water (1 ml), 4N NaOH (1 ml), and water (3 ml). The mixture was stirred for 10 min then filtered through hyflo and evaporated in vacuo. The residue was purified by column chromatography (SiO$_2$; 5% MeOH in CH$_2$Cl$_2$+0.5% NH$_3$), and the oxalate salt formed from EtOH/Et$_2$O to afford 1.88 g (4.8 mmol; 53%) of 3-(1-methylpiperidin-3-ylmethyl)-2-phenyl-1H-indole hydrogen oxalate as a white solid (Found: C, 69.09; H, 6.53; N, 7.05; C$_{23}$H$_{26}$N$_2$O$_4$.0.25H$_2$O requires C, 69.24; H, 6.70; N, 7.05%); mp 234° C. (from EtOH/Et$_2$O); δ$_H$(360 MHz; DMSO-d$_6$) 0.97–1.14 (1H, m, aliphatic), 1.47–1.74 (3H, m, aliphatics), 2.10–2.26 (1H, m, aliphatic), 2.62 (3H, s, CH$_3$), 2.63–2.85 (4H, m, aliphatics), 3.18–3.30 (2H, m, aliphatics), 7.01 (1H, t, J 7.6 and 7.2, indole H5), 7.11 (1H, t, J 7.6 and 7.5, indole H6), 7.35–7.40 (2H, m, aromatics), 7.49–7.57 (3H, m, aromatics), 7.63 (2H, d, J 7.4, aromatics), 11.32 (1H, br s, NH); m/z (ES$^+$) 305 (M$^+$+H, 100%).

EXAMPLE 2

3-(1-Methylpyrrolidin-3-ylmethyl)-2-phenyl-1H-indole hydrogen oxalate

By substantially following the procedures of Example 1, utilising N-benzyloxycarbonylpyrrolidine-3-carboxylic acid in place of N-benzyloxycarbonylnipecotic acid, was prepared the title compound as a white solid. (Found: C, 65.87; H, 6.43; N, 6.83; $C_{22}H_{24}N_2O_4 \cdot 1.2H_2O$ requires C, 65.72; H, 6.62; N, 6.97%); mp 80° C. (from $EtOH/Et_2O$); $\delta_H$ (360 MHz; DMSO-$d_6$) 1.58–1.70 (1H, m, aliphatic), 1.86–2.00 (1H, m, aliphatic), 2.70 (4H, m, $CH_3$ and aliphatic), 2.90–3.00 (1H, m, aliphatic), 3.05 (2H, d, J 7.3, indole $CH_2$), 3.10–3.34 (2H, m, aliphatics), 7.03 (1H, t, J 7.4 and 7.3, indole H5), 7.11 (1H, t, J 7.7 and 7.3, indole H6), 7.33–7.42 (2H, m, aromatics), 7.46–7.56 (2H, m, aromatics), 7.60–7.68 (3H, m, aromatics), 11.28 (1H, br s, NH); m/z ($ES^+$) 291 ($M^+$+H, 100%).

EXAMPLE 3

3-(1-Methylpyrrolidin-2(R)-ylmethyl)-2-phenyl-1H-indole

By substantially following the procedures of Example 1, utilising N-benzyloxycarbonyl-D-proline in place of N-benzyloxycarbonylnipecotic acid, was prepared the title compound as a white solid. (Found: C, 82.82; H, 7.63; N, 9.61; $C_{20}H_{22}N_2$ requires C, 82.72; H, 7.64; N, 9.65%); mp 132° C. (from $Et_2O$/hexanes); $[\alpha]_D^{22}$ +100.1 (c 1.0 in $CDCl_3$); $\delta_H$ (400 MHz; $CDCl_3$) 1.33–1.44 (1H, m, aliphatic), 1.44–1.55 (1H, m, aliphatic), 1.55–1.72 (2H, m, aliphatics), 2.08–2.18 (1H, m, aliphatic), 2.35–2.50 (4H, m, $CH_3$ and aliphatic), 2.84 (1H, dd, J 13.8 and 9.9, indole $CH_AH_B$), 3.04 (1H, m, pyrrolidine H2), 3.31 (1H, dd, J 13.8 and 3.9, indole $CH_ACH_B$), 7.13 (1H, t, J 7.8 and 7.2, indole H6), 7.20 (1H, t, J 7.8 and 7.2, indole H5), 7.33–7.38 (2H, m, aromatics), 7.45 (2H, t, J 7.8 and 7.4, aromatics), 7.59 (2H, d, J 7.2, aromatics), 7.65 (1H, d, J 7.8, indole H4), 8.05 (1H, br s, NH); m/z ($ES^+$) 291 ($M^+$+H, 100%).

EXAMPLE 4

3-(1-Methylpyrrolidin-2(S)-ylmethyl)-2-phenyl-1H-indole

By substantially following the procedures of Example 1, utilising N-benzyloxycarbonyl-L-proline in place of N-benzyloxycarbonylnipecotic acid, was prepared the title compound as a white solid. (Found: C, 82.69; H, 7.23; N, 9.60; $C_{20}H_{22}N_2$ requires C, 82.72; H, 7.64; N, 9.65%); mp 133° C. (from $Et_2O$/hexanes); $[\alpha]_D^{22}$ –105.0 (c 1.0 in $CDCl_3$); $\delta_H$ (360 MHz; $CDCl_3$) 1.34–1.45 (1H, m, aliphatic), 1.48–1.56 (1H, m, aliphatic), 1.58–1.73 (2H, m, aliphatics), 2.11–2.18 (1H, m, aliphatic), 2.42–2.52 (4H, m, $CH_3$ and aliphatic), 2.84 (1H, dd, J 13.8 and 9.9, indole $CH_AH_B$), 3.04–3.10 (1H, m, pyrrolidine H2), 3.31 (1H, dd, J 13.8 and 4.0, indole $CH_ACH_B$), 7.11–7.15 (1H, m, indole H6), 7.17–7.22 (1H, t, J 7.8 and 7.2, indole H5), 7.33–7.40 (2H, m, aromatics), 7.42–7.47 (2H, m, aromatics), 7.59 (2H, dd, J 8.5 and 1.4, aromatics), 7.66 (1H, d, J 8.1, indole H4), 8.03 (1H, br s, NH); m/z ($ES^+$) 291 ($M^+$+H, 100%).

EXAMPLE 5

2-Methyl-3-(2-phenyl-1H-indol-3-ylmethyl)-2-azabicyclo[2.2.2]octane hydrogen oxalate By substantially following the procedures of Example 1, utilising 2-azabicyclo[2.2.2]octane-2,3-dicarboxylic acid-2-benzyl ester in place of N-benzyloxycarbonylnipecotic acid, was prepared the title compound as a white solid. (Found: C, 72.26; H, 7.29; N, 7.13; $C_{25}H_{28}N_2O_4 \cdot 0.8H_2O$ requires C, 72.44; H, 7.56; N, 7.35%); mp 193° C. (from $EtOH/Et_2O$); $\delta_H$ (360 MHz; DMSO-$d_6$) 1.12–1.56 (6H, m, aliphatics), 1.90–2.06 (1H, m, aliphatic), 2.16–2.30 (1H, m, aliphatic), 2.87 (3H, s, $CH_3$), 3.00–3.11 (1H, m, aliphatic), 3.11–3.22 (1H, m, aliphatic), 3.30–3.50 (4H, m, aliphatics), 7.06 (1H, t, J 7.7 and 7.1, indole H5), 7.14 (1H, t, J 7.4 and 7.4, indole H6), 7.39–7.45 (2H, m, aromatics), 7.54 (2H, t, J 7.7 and 7.4, aromatics), 7.58–7.66 (3H, m, aromatics), 10.48 (1H, br s, $NH^+$), 11.47 (1H, br s, NH); m/z ($ES^+$) 331 ($M^{30}$+H, 100%).

EXAMPLE 6

3-(2-Methyl-2-azabicyclo[2.2.1]hept-3-ylmethyl)-2-phenyl-1H-indole hydrogen chloride By substantially following the procedures of Example 1, utilising 2-azabicyclo[2.2.1]heptane-2,3-dicarboxylic acid-2-benzyl ester in place of N-benzyloxycarbonylnipecotic acid, was prepared the title compound as a white solid. (Found: C, 72.16; H, 7.40; N, 7.50; $C_{23}H_{25}N_2Cl \cdot 0.75H_2O$ requires C, 72.11; H, 7.29; N, 7.65%); mp 176° C. (from $MeOH/Et_2O$); $\delta_H$ (360 MHz; DMSO-$d_6$) 1.13–1.24 (1H, m, aliphatic), 1.40–1.62 (3H, m, aliphatics), 1.80–1.90 (1H, m, aliphatic), 2.00–2.08 (2H, m, aliphatics), 2.80 (3H, s, $CH_3$), 2.96–3.04 (1H, m, aliphatic), 3.14–3.36 (4H, m, aliphatics), 3.83 (1H, m, aliphatic), 7.06 (1H, t, J 7.8 and 6.9, indole H5), 7.13 (1H, t, J 8.2 and 7.8, indole H6), 7.39–7.45 (2H, m, aromatics), 7.54 (2H, t, J 7.8 and 7.5, aromatics), 7.62–7.67 (3H, m, aromatics), 10.67 (1H, br s, $NH^+$), 11.47 (1H, br s, NH); m/z ($ES^+$) 317 ($M^+$+H, 100%).

EXAMPLE 7

3-(1,5-Dimethyl-cis-pyrrolidin-2-ylmethyl)-2-phenyl-1H-indole hydrogen oxalate By substantially following the procedures of Example 1, utilising N-benzyloxycarbonyl-cis-5-methylproline in place of N-benzyloxycarbonylnipecotic acid, was prepared the title compound as a white solid. (Found: C, 69.56; H, 6.61; N, 6.98; $C_{23}H_{26}N_2O_4 \cdot 0.1H_2O$ requires C, 69.51; H, 6.66; N, 7.07%); mp 183° C. (from $EtOH/Et_2O$); $\delta_H$ (360 MHz; DMSO-$d_6$) 1.30 (3H, d, J 6.4, $CH_3$), 1.46–1.70 (3H, m, aliphatics), 1.90–2.04 (1H, m, aliphatic), 2.84 (3H, s, $NCH_3$), 3.18–3.31 (2H, m, aliphatics), 3.43–3.58 (2H, m, aliphatics), 7.05 (1H, t, J 7.7 and 7.1, indole H5), 7.13 (1H, t, J 7.7 and 7.3, indole H6), 7.38–7.43 (2H, m, aromatics), 7.53 (2H, t, J 7.7 and 7.5, aromatics), 7.64–7.69 (3H, m, aromatics), 11.38 (1H, br s, NH); m/z ($ES^+$) 305 ($M^+$+H, 100%).

EXAMPLE 8

3-(1,4-Dimethylpiperazin-2(S)-ylmethyl)-2-phenyl-1H-indole dihydrochloride

By substantially following the procedures of Example 1, utilising di-N-benzyloxycarbonylpiperazine-2(R)-carboxylic acid in place of N-benzyloxycarbonylnipecotic acid, the title compound was prepared as a white solid. (Found: C, 63.90; H, 6.92; N, 10.57; $C_{21}H_{27}Cl_2N_2$ requires C, 64.28; H, 6.94; N, 10.71%); mp 253° C. (from $Et_2O$/MeOH); $[\alpha]D^{22}$+35.4 (c 1.0 in MeOH); $\delta_H$ (360 MHz; $D_2O$) 2.41 (4H, m, $CH_3$ and aliphatic), 2.61 (3H, s, $CH_3$), 2.70–2.77 (2H, m, aliphatics), 2.82 (1H, br d, J 13.4, aliphatic), 2.93 (2H, br d, J 10.4, aliphatics), 3.19 (2H, br d, J 10.1, aliphatics), 3.59 (1H, d, J 9.9, aliphatic), 7.25 (1H, t, J 7.9 and 7.0, indole H6), 7.32 (1H, t, J 7.9 and 7.1, indole H5), 7.51–7.66 (6H, m, aromatics), 7.42–7.47 (2H, m, aromatics), 7.69 (1H, d, J 7.9, indole H4); m/z ($ES^{30}$) 320 ($M^{30}$+H, 100%).

EXAMPLE 9

7-Chloro- 3-(1,4-dimethylpiperazin-2(S)-ylmethyl)-2-phenyl-1H-indole dihydrochloride By substantially following the procedures of Example 1, utilising di-N-benzyloxycarbonylpiperazine-2(R)- carboxylic acid in place of N-benzyloxycarbonylnipecotic acid and 7-chloro-2-phenylindole in place of 2-phenylindole, was prepared the title compound as a white solid. (Found: C, 57.69; H, 6.11; N, 9.56; $C_{21}H_{24}Cl_3N_2.0.6H_2O$ requires C, 57.64; H, 6.27; N, 9.60%); mp 260° C. (from EtOH); $[\alpha]D^{22}$+25.2 (c 1.0 in MeOH); $\delta_H$ (400 MHz; $D_2O$) 2.38 (4H, m, $CH_3$ and aliphatic), 2.58 (3H, s, $CH_3$), 2.70–2.88 (5H, m, aliphatics), 3.16–3.21 (2H, m, aliphatics), 3.50 (1H, m, aliphatic), 7.19 (1H, t, J 7.9 and 7.8, indole H5), 7.32 (1H, dd, J 7.6 and 0.6, indole H6), 7.51–7.55 (1H, m, aromatic), 7.57–7.63 (8H, m, aromatics); m/z ($ES^{30}$) 353 ($M^+$+H, 100%).

EXAMPLE 10

3-(4-Methylmorpholin-3-ylmethyl)-2-phenyl-1H,-indole hydrogen oxalate

By substantially following the procedures of Example 1, utilising N-benzyloxycarbonylmorpholine-3-carboxylic acid in place of N-benzyloxycarbonylnipecotic acid, was prepared the title compound as a white solid. (Found: C, 66.63; H, 5.95; N, 6.86; $C_{22}H_{24}N_2O_5$ requires C, 66.65; H, 6.10; N, 7.07%); mp 255° C. (from $EtOH/Et_2O$); $\delta_H$ (360 MHz; DMSO-$d_6$) 2.76 (3H, s, $CH_3$), 2.81–2.91 (1H, m, aliphatic), 2.94–3.05 (1H, m, aliphatic), 3.07 (2H, m, aliphatics), 3.23–3.33 (1H, m, aliphatic), 3.36–3.43 (1H, m, aliphatic), 3.43–3.52 (1H, m, aliphatic), 3.57–3.68 (1H, m, aliphatic), 3.75 (1H, br d, J 12.2, aliphatic), 7.06 (1H, t, J 7.8 and 7.1, indole H5), 7.14 (1H, t, J 7.7 and 7.2, indole H6), 7.37–7.44 (2H, m, aromatics), 7.53 (2H, t, J 7.8 and 7.4, aromatics), 7.61 (1H, d, J 7.8, indole H4), 7.66 (2H, d, J 7.2, aromatics), 11.35 (1H, br s, NH); m/z ($ES^{30}$) 307 ($M^{30}$+H, 100%).

EXAMPLE 11

3-[1-(2-Phenylethyl)piperidin-3-ylmethyl]-2-phenyl-1H-indole hydrogen oxalate A. (2-Phenyl-1H-indol-3-yl)piperidin-3-ylmethanone A solution of 11.6 g (26.5 mmol) of 3-(2-phenyl-1H-indol-3-ylcarbonyl)piperidine-1-carboxylic acid benzyl ester and 6.4 g (79.5 mmol) of 1,4-cyclohexadiene in ethanol under an atmosphere of nitrogen was charged with 1 g of 10% palladium on carbon. The mixture was heated under reflux for 2 hr, after which it was cooled and filtered to remove the catalyst, and the filtrate evaporated in vacuo to afford 7.5 g (24.7 mmol; 93%) of (2-phenyl-1H-indol-3-yl) piperidin-3-ylmethanone as a clear oil. $\delta_H$ (360 MHz; $CDCl_3$) 1.02–1.15 (1H, m, aliphatic), 1.51–1.70 (2H, m, aliphatics), 1.73–1.84 (2H, m, aliphatics), 2.51–2.62 (1H, m, aliphatic), 2.78–2.89 (3H, m, aliphatics), 2.92–3.02 (1H, m, aliphatic), 7.22–7.28 (2H, m, aromatics), 7.36–7.47 (3H, m, aromatics), 7.50–7.56 (2H, m, aromatics), 8.21–8.27 (1H, m, aromatic), 10.46 (1H, br s, NH); m/z ($ES^+$) 305 ($M^+$+H, 100%).

B. 2-Phenyl-3-(piperidin-3-ylmethyl)-1H-indole

To a solution of 7.5 g (24.7 mmol) of (2-phenyl-1H-indol-3-yl)piperidin-3-ylmethanone in anhydrous tetrahydrofuran (100 ml) under an atmosphere of nitrogen was added cautiously over 5 min a solution of lithium aluminium hydride (50 ml of a 1M solution in tetrahydrofuran, 50 mmol) at 0° C. The mixture was heated at reflux for 3 hr, after which it was cooled and quenched by the careful addition of water (2 ml), 4N NaOH (2 ml), and water (6 ml). The mixture was stirred for 10 min then filtered through hyflo and evaporated in vacuo to afford 5.6 g (19.3 mmol; 78%) of 2-phenyl-3-(piperidin-3-ylmethyl)-1H-indole as a clear oil. $\delta_H$ (360 MHz; $CDCl_3$) 1.00–1.13 (1H, m, aliphatic), 1.28–1.40 (1H, m, aliphatic), 1.44–1.62 (2H, m, aliphatics), 1.74–1.86 (1H, m, aliphatic), 2.27 (1H, t, J 10.3, aliphatic), 2.44–2.52 (1H, m, aliphatic), 2.75 (2H, dd, J 7.2 and 3.3, aliphatics), 2.91–3.03 (2H, m, aliphatics), 7.12 (1H, t, J 7.9 and 7.1, indole H5), 7.19 (1H, t, J 7.9 and 7.0, indole H6), 7.32–7.39 (2H, m, aromatics), 7.42–7.50 (2H, m, aromatics), 7.54 (2H, dd, J 8.5 and 1.4, aromatics), 7.62 (1H, d, J 7.1, indole H4), 8.10 (1H, br s, NH); m/z ($ES^+$) 291 ($M^+$+H, 100%).

C. 3-[1-(2-Phenylethyl)piperidin-3-ylmethyl]-2-phenyl-1H-indole hydrogen oxalate To a solution of 1 g (3.4 mmol) of 2-phenyl-3-(piperidin-3-ylmethyl)-1H-indole and 565 μl (4.1 mmol) of phenethyl bromide in propan-2-ol (25 ml) was added potassium carbonate (522 mg, 4.1 mmol). The mixture was heated under reflux for 15 hr under an atmosphere of nitrogen, after which it was cooled and evaporated in vacuo. The residue was partitioned between water (50 ml) and EtOAc (50 ml), the organic layer separated, and the aqueous layer extracted with EtOAc (2×40 ml). The combined EtOAc layers were washed with water (50 ml), saturated sodium chloride (50 ml), dried over $MgSO_4$, and evaporated in vacuo. The residue was purified by column chromatography ($SiO_2$; 4% MeOH in $CH_2Cl_2$+0.5% $NH_3$ then 6% MeOH in $CH_2Cl_2$+0.5% $NH_3$), and the oxalate salt formed from $EtOH/Et_2O$ to afford 510 mg (1.1 mmol; 31%) of 3-[1-(2-phenylethyl)piperidin-3-ylmethyl]-2-phenyl-1H-indole hydrogen oxalate as a white solid. (Found C, 73.20; H, 6.46; N, 5.69; $C_{30}H_{32}N_2O_4.0.3H_2O$ requires C, 73.54; H, 6.71; N, 5.72%); mp 128° C. (from $EtOH/Et_2O$); $\delta_H$ (360 MHz; DMSO-$d_6$) 1.00–1.16 (1H, m, aliphatic), 1.50–1.78 (2H, m, aliphatics), 2.12–2.28 (1H, m, aliphatic), 2.54–2.68 (1H, m, aliphatic), 2.68–2.98 (5H, m, aliphatics), 3.06–3.22 (2H, m, aliphatics), 3.30–3.46 (2H, m, aliphatics), 7.02 (1H, t, J 7.7 and 7.1, indole H5), 7.11 (1H, t, J 7.7 and 7.5, indole H6), 7.19–7.25 (3H, m, aromatics), 7.29–7.33 (2H, m, aromatics), 7.37–7.41 (2H, m, aromatics), 7.52 (2H, t, J 7.8 and 7.5, aromatics), 7.58 (1H, d, J 7.8, aromatic), 7.63–7.66 (2H, m, aromatics), 11.29 (1H, br s, NH); m/z ($ES^+$) 395 ($M^+$+H, 100%).

EXAMPLE 12

3-(1-Benzylpyrrolidin-2-ylmethyl)-2-phenyl-1H-indole hydrogen oxalate

By substantially following the procedures of Example 11, utilising 2-(2-phenyl-1H-indol-3-ylcarbonyl)pyrrolidine-1-carboxylic acid benzyl ester in place of 3-(2-phenyl-1H-indol-3-ylcarbonyl)piperidine-1-carboxylic acid benzyl ester, was prepared the title compound as a white solid. (Found: C, 65.87; H, 6.43; N, 6.83; $C_{28}H_{28}N_2O_4$ requires C, 65.72; H, 6.62; N, 6.97%); mp 210° C. (from $EtOH/Et_2O$); $\delta_H$ (360 MHz; DMSO-$d_6$) 1.43–1.59 (1H, m, aliphatic), 1.62–1.80 (3H, m, aliphatics), 2.89–3.03 (1H, m, aliphatic), 3.16–3.30 (2H, m, aliphatics), 3.42 (1H, dd, J 14.1 and 4.3, indole $CH_AH_B$), 3.49–3.62 (1H, m, aliphatic), 4.11 (1H, d, J 12.9, $PhCH_AH_B$), 4.51 (1H, d, J 12.9, $PhCH_AH_B$), 7.02 (1H, t, J 7.6 and 7.1, indole H5), 7.12 (1H, t, J 7.8 and 7.1, indole H6), 7.36–7.55 (10H, m, aromatics), 7.65 (2H, d, J 7.2, aromatics); m/z ($ES^+$) 367 ($M^+$+H, 100%).

EXAMPLE 13

3-[1-(2-Phenylethyl)pyrrolidin-2-ylmethyl]-2-phenyl-1H-indole hydrogen oxalate By substantially following the procedures of Example 11, utilising 2-(2-phenyl-1H-indol-3-ylcarbonyl)pyrrolidine-1-carboxylic acid benzyl ester in place of 3-(2-phenyl-1H-indol-3-ylcarbonyl)piperidine-1-carboxylic acid benzyl ester, was prepared the title compound as a white solid. (Found: C, 74.22; H, 6.44; N, 5.71; $C_{29}H_{30}N_2O_4$ requires C, 74.02; H, 6.43; N, 5.95%); mp 182° C. (from $EtOH/Et_2O$); $\delta_H$ (360 MHz; DMSO-$d_6$) 1.50–1.67 (1H, m, aliphatic), 1.69–1.90 (3H, m, aliphatics), 2.86–3.04 (2H, t, J 8.2, PhCH$_2$CH$_2$), 3.06–3.22 (2H, m, aliphatics), 3.22–3.35 (1H, m, indole CH$_A$H$_B$), 3.46–3.70 (4H, m, aliphatics), 7.04 (1H, t, J 7.7 and 7.1, indole H5), 7.13 (1H, t, J 7.7 and 7.3, indole H6), 7.21–7.57 (9H, m, aromatics), 7.62–7.73 (3H, m, aromatics); m/z (ES$^+$) 381 (M$^+$+H, 100%).

EXAMPLE 14

2-Phenyl-3-[1-(3-phenylpropyl)pyrrolidin-2(R)-ylmethyl]-1H-indole hydrogen oxalate By substantially following the procedures of Example 11, utilising 2(R)-(2-phenyl-1H-indol-3-ylcarbonyl)pyrrolidine-1-carboxylic acid benzyl ester in place of 3-(2-phenyl-1H-indol-3-ylcarbonyl)piperidine-1-carboxylic acid benzyl ester, was prepared the title compound as a white solid. (Found: C, 74.72; H, 6.52; N, 5.79; C$_{30}$H$_{32}$N$_2$O$_4$ requires C, 74.36; H, 6.66; N, 5.78%); mp 146° C. (from EtOH/Et$_2$O); [α]$_D^{23}$+8.0 (c 1.0 in CHCl$_3$); δ$_H$ (360 MHz; DMSO-d$_6$) 1.53–1.70 (1H, m, aliphatic), 1.70–1.90 (3H, m, aliphatics), 1.90–2.08 (2H, m, aliphatics), 2.58–2.78 (2H, m, aliphatics), 2.90–3.14 (2H, m, aliphatics), 3.25–3.46 (2H, m, aliphatics), 3.46–3.70 (3H, m, aliphatics), 7.11 (1H, t, J 7.5 and 7.2, indole H5), 7.20 (1H, t, J 7.7 and 7.3, indole H6), 7.25–7.34 (3H, m, aromatics), 7.34–7.42 (2H, m, aromatics), 7.42–7.50 (2H, m, aromatics), 7.55 (2H, t, J 7.6 and 7.3, aromatics), 7.66–7.34 (3H, m, aromatics), 11.46 (1H, br s, NH); m/z (ES$^+$) 396 (M$^+$+H, 100%).

EXAMPLE 15

3-(1-Benzylpyrrolidin-3-ylmethyl)-2-phenyl-1H-indole hydrogen oxalate

By substantially following the procedures of Example 11, utilising 3-(2-phenyl-H-indol-3-ylcarbonyl)pyrrolidine-1-carboxylic acid benzyl ester in place of 3-(2-phenyl-1H-indol-3-ylcarbonyl)piperidine-1-carboxylic acid benzyl ester, was prepared the title compound as a tan solid. (Found: C, 71.07; H, 6.01; N, 5.95; C$_{28}$H$_{28}$N$_2$O$_4$.0.9H$_2$O requires C, 71.14; H, 6.35; N, 5.93%); mp 95° C. (from EtOH/Et$_2$O); δ$_H$ (360 MHz; DMSO-d$_6$) 1.56–1.60 (1H, m, aliphatic), 1.86–2.00 (1H, m, aliphatic), 3.60–3.75 (1H, m, aliphatic), 3.80–3.92 (1H, m, aliphatic), 3.04 (2H, d, J 7.3, indole CH$_2$), 3.07–3.28 (3H, m, aliphatics), 4.22 (2H, s, PhCH$_2$); 7.01 (1H, t, J 7.6 and 7.2, indole H5), 7.10 (1H, t, J 7.6 and 7.4, indole H6), 7.32–7.47 (7H, m, aromatics), 7.51 (2H, t, J 7.8 and 7.4, aromatics), 7.60–7.65 (3H, m, aromatics), 11.25 (1H, br s, NH); m/z (ES$^+$) 367 (M$^+$+H, 100%).

EXAMPLE 16

3-[1-(2-Phenylethyl)pyrrolidin-3-ylmethyl]-2-phenyl-1H-indole hydrogen oxalate By substantially following the procedures of Example 11, utilising 3-(2-phenyl-1H-indol-3-ylcarbonyl)pyrrolidine-1-carboxylic acid benzyl ester in place of 3-(2-phenyl-1H-indol-3-ylcarbonyl)piperidine-1-carboxylic acid benzyl ester, was prepared the title compound as a beige solid. (Found: C, 69.99; H, 6.26; N, 5.86; C$_{29}$H$_{30}$N$_2$O$_4$.1.4H$_2$O requires C, 70.26; H, 6.67; N, 5.65%); mp 100° C. (from EtOH/Et$_2$O); δ$_H$ (360 MHz; DMSO-d$_6$) 1.56–1.70 (1H, m, aliphatic), 1.84–2.00 (2H, m, aliphatics), 2.80–3.12 (5H, m, aliphatics), 3.16–3.50 (5H, m, aliphatics), 3.60–3.76 (1H, m, aliphatic), 7.30 (1H, t, J 7.5 and 7.2, indole H5), 7.12 (1H, t, J 7.5 and 7.3, indole H6), 7.21–7.25 (3H, m, aromatics), 7.29–7.33 (2H, m, aromatics), 7.37–7.41 (2H, m, aromatics), 7.52 (2H, t, J 7.6 and 7.4, aromatics), 7.64–7.68 (3H, m, aromatics), 11.28 (1H, br s, NH); m/z (ES$^+$) 381 (M$^+$+H, 100%).

EXAMPLE 17

3-(1-Methylpiperidin-2(R)-ylmethyl)-2-phenyl-1H-indole

A. (2-Phenyl-1H-indol-3-yl)piperidin-2(R)-ylmethanone

A solution of 3 g (11.4 mmol) of N-benzyloxycarbonyl-D-pipecolinic acid in anhydrous dichloromethane (25 ml) under an atmosphere of nitrogen was treated with oxalyl chloride (1.5 ml, 17 mmol) followed by 2 drops of N,N-dimethylformamide. The reaction mixture was stirred at room temperature for 90 min at which time the dichloromethane was evaporated in vacuo. The residue was dissolved in anhydrous toluene (25 ml) and the resulting solution evaporated in vacuo. The residue was dissolved in anhydrous benzene (20 ml) to give Solution A.

A solution of 4.4 g (22.8 mmol) of 2-phenylindole in anhydrous benzene (100 ml) under an atmosphere of nitrogen was added using a cannula to a solution of ethylmagnesium bromide (7.6 ml of a 3M solution in diethyl ether, 22.8 mmol) and the resulting mixture stirred at room temperature for 15 min to give Solution B.

Solution A was added in one portion to rapidly stirred solution B and the resulting mixture stirred at room temperature for 30 min. The reaction was quenched by the addition of saturated ammonium chloride solution (100 ml). The organic layer was separated, dried over MgSO$_4$ and evaporated in vacuo. The residue was purified by flash chromatography (SiO$_2$; 5% MeOH in CH$_2$Cl$_2$+0.5% NH$_3$) to afford 2.4 g (7.9 mmol; 69%) of (2-phenyl-1H-indol-3-yl)piperidin-2(R)-ylmethanone as an orange solid. δ$_H$ (360 MHz; DMSO-d$_6$) 1.00–1.17 (1H, m, aliphatic), 1.54–1.71 (1H, m, aliphatic), 1.74–1.91 (3H, m, aliphatics), 2.00–2.12 (1H, m, aliphatic), 2.76–2.90 (1H, m, aliphatic), 3.40–3.52 (1H, m, aliphatic), 4.22–4.34 (1H, m, aliphatic), 7.44–7.58 (2H, m, aromatics), 7.71–7.90 (4H, m, aromatics), 7.90–8.07 (2H, m, aromatics), 8.36–8.46 (1H, m, aromatic); m/z (ES$^+$) 305 (M$^+$+H, 100%).

B. 2-Phenyl-3-(Piperidin-2(R)-ylmethyl)-1H-indole

To a suspension of 2.4 g (7.9 mmol) of (2-phenyl-1H-indol-3-yl)piperidin-2(R)-ylmethanone in anhydrous tetrahydrofuran (15 ml) under an atmosphere of nitrogen was added cautiously over 5 min a solution of lithium aluminium hydride (12.5 ml of a 1M solution in tetrahydrofuran, 12.5 mmol) at 0° C. The mixture was heated under reflux for 13 hr, after which it was cooled and quenched by careful addition of water (0.5 ml), 4N NaOH (0.5 ml), and water (1.5 ml). The mixture was stirred for 10 min then filtered through hyflo and evaporated in vacuo to afford 1.2 g (4.1 mmol; 52%) of 2-phenyl-3-(piperidin-2(R)-ylmethyl)-1H-indole as a yellow oil. δ$_H$ (360 MHz; CDCl$_3$) 1.09–1.26 (1H, m, aliphatic), 1.38–1.52 (1H, m, aliphatic), 1.60–1.74 (3H, m, aliphatics), 1.74–1.90 (1H, m, aliphatic), 2.67–2.80 (1H, m, aliphatic), 3.12–3.25 (1H, m, aliphatic), 3.28–3.38 (2H, m, aliphatics), 3.69 (1H, dd, J 13.8 and 4.2, indole CH$_A$H$_B$), 7.06–7.21 (2H, m, aromatics), 7.29–7.49 (4H, m, aromatics), 7.58 (1H, d, J 7.2, aromatics), 7.81 (1H, d, J 7.6, aromatic), 9.15 (1H, br s, NH); m/z (ES$^+$) 291 (M$^+$+H, 100%).

C. 3-(1-Methylpiperidin-2(R)-ylmethyl)-2-phenyl-1H-indole

To a solution of 1.1 g (3.8 mmol) of 2-phenyl-3-(piperidin-2(R)-ylmethyl)-1H-indole and 238 mg (3.8 mmol) of sodium cyanoborohydride in methanol (20 ml) at 0° C. was added a solution of formaldehyde (527 mg of a 37% w/w aqueous solution) and glacial acetic acid (0.5 ml, 8.7 mmol) in methanol (10 ml). After stirring at room temperature for 3 hr the reaction was evaporated in vacuo. The residue was partitioned between saturated potassium carbonate (20 ml) and EtOAc (20 ml), the organic layer separated, and the aqueous layer extracted with EtOAc (2×20 ml). The combined EtOAc layers were washed with water (50 ml), saturated sodium chloride (50 ml), dried over MgSO$_4$ and evaporated in vacuo. The residue was purified by column chromatography (SiO$_2$; 5% MeOH in CH$_2$Cl$_2$+ 0.5% NH$_3$) and the product recrystallised from Et$_2$O/ hexanes to afford 210 mg (0.7 mmol; 18%) of 3-(1-methylpiperidin-2(R)-ylmethyl)-2-phenyl-1H-indole as a white solid. (Found: C, 81.50; H, 7.98; N, 9.14; C$_{21}$H$_{24}$N$_2$.0.25H$_2$O requires C, 81.64; H, 7.99; N, 9.07%); mp 150° C. (from Et$_2$O/hexane); [α]D$^{23}$+80.0 (c 1.0 in CHCl$_3$); δ$_H$ (360 MHz; CDCl$_3$) 0.96–1.14 (2H, m, aliphatics), 1.44–1.58 (4H, m, aliphatics), 2.06–2.16 (1H, m, aliphatic), 2.21–2.32 (1H, m, aliphatic), 2.46 (3H, s, CH$_3$), 2.76–2.89 (2H, m, aliphatics), 3.47 (1H, dd, J 13.8 and 3.8, indole CH$_A$H$_B$), 7.14 (1H, m, indole H5), 7.20 (1H, m, indole H6), 7.33–7.38 (2H, m, aromatics), 7.43–7.47 (2H, m, aromatics), 7.57 (2H, d, J 7.1, aromatics), 7.65 (1H, d, J 7.8, aromatic), 8.05 (1H, br s, NH); m/z (ES$^+$) 305 (M$^+$+H, 100%).

EXAMPLE 18

3-(1-Methylpiperidin-2(S)-ylmethyl)-2-phenyl-1H-indole

By substantially following the procedures of Example 17, utilising N-benzyloxycarbonyl-L-pipecolinic acid in place of N-benzyloxycarbonyl-D-pipecolinic acid, the title compound was prepared as a white solid. (Found: C, 80.62; H, 7.39; N, 8.96; C$_{21}$H$_{24}$N$_2$ requires C, 80.42; H, 7.71; N, 8.93% corrected for 3% ash); mp 135° C. (from Et$_2$O/ hexane); [α]D$^{23}$ −78.0 (c 1.0 in CHCl$_3$); δ$_H$ (360 MHz; CDCl$_3$) 0.94–1.17 (2H, m, aliphatics), 1.42–1.58 (4H, m, aliphatics), 2.04–2.18 (1H, m, aliphatic), 2.22–2.34 (1H, m, aliphatic), 2.46 (3H, s, CH$_3$), 2.74–2.90 (2H, m, aliphatics), 3.47 (1H, dd, J 13.8 and 3.8, indole CH$_A$H$_B$), 7.14 (1H, t, J 7.9 and 7.0, indole H5), 7.20 (1H, t, J 7.9 and 6.9, indole H6), 7.33–7.37 (2H, d, J 7.6, aromatics), 7.46 (2H, t, J 7.8 and 7.2, aromatics), 7.57 (2H, m, aromatics), 7.65 (1H, d, J 7.8, aromatic), 8.04 (1H, br s, NH); m/z (ES$^+$) 305 (M$^+$+H, 100%).

EXAMPLE 19

3-(1-Methylazepin-2(R)-ylmethyl)-2-phenyl-1H-indole hydrochloride

By substantially following the procedures of Example 17, utilising N-benzyloxycarbonyl-(R)-perhydro-2-azepinecarboxylic acid in place of N-benzyloxycarbonyl-D-pipecolinic acid, the title compound was prepared as a white solid. (Found: C, 71.64; H, 7.75; N, 7.62; C$_{22}$H$_{27}$N$_2$Cl.0.8H$_2$O requires C, 71.55; H, 7.81; N, 7.58%); mp 145° C. (from MeOH/Et$_2$O); [α]D$^{23}$ −9.1 (c 1.0 in CHCl$_3$); m/z (ES$^+$) 319 (M$^+$+H, 100%); δ$_H$ (360 MHz; CDCl$_3$ of free base) 1.11–1.23 (1H, m, aliphatic), 1.30–1.69 (7H, m, aliphatics), 2.49 (3H, s, CH$_3$), 2.70–2.80 (1H, m, aliphatic), 2.80–3.00 (3H, m, aliphatics), 3.17 (1H, dd, J 13.7 and 3.8, aliphatic), 7.13 (1H, m, indole H5), 7.20 (1H, m, indole H6), 7.33–7.38 (2H, m, aromatics), 7.43–7.48 (2H, m, aromatics), 7.60 (2H, dd, J 8.5 and 1.4, aromatics), 7.65 (1H, d, J 7.9, aromatic), 8.01 (1H, br s, NH).

EXAMPLE 20

3-(1-Methylazepin-2(S)-ylmethyl)-2-phenyl-1H-indole hydrochloride

By substantially following the procedures of Example 17, utilising N-benzyloxycarbonyl-(S)-perhydro-2-azepinecarboxylic acid in place of N-benzyloxycarbonyl-D-pipecolinic acid, the title compound was prepared as a white solid. (Found: C, 70.85; H, 7.88; N, 7.55; C$_{22}$H$_{27}$N$_2$Cl.H$_2$O requires C, 70.85; H, 7.84; N, 7.51%); mp 148° C. (from MeOH/Et$_2$O); [α]D$^{23}$+8.6 (c 1.0 in CHCl$_3$); m/z (ES$^+$) 319 (M$^+$+H, 100%); δ$_H$ (360 MHz; CDCl$_3$ of free base) 1.11–1.23 (1H, m, aliphatic), 1.30–1.69 (7H, m, aliphatics), 2.49 (3H, s, CH$_3$), 2.70–2.80 (1H, m, aliphatic), 2.80–3.00 (3H, m, aliphatics), 3.17 (1H, dd, J 13.7 and 3.8, aliphatic), 7.13 (1H, m, indole H5), 7.20 (1H, m, indole H6), 7.33–7.38 (2H, m, aromatics), 7.43–7.48 (2H, m, aromatics), 7.60 (2H, dd, J 8.5 and 1.4, aromatics), 7.65 (1H, d, J 7.9, aromatic), 8.01 (1H, br s, NH).

EXAMPLE 21

3-(1-Ethylpiperidin-2-ylmethyl)-2-phenyl-1H-indole hydrogen oxalate

By substantially following the procedures of Example 11.C, utilising 2-phenyl-3-(piperidin-2-ylmethyl)-1H-indole in place of 2-phenyl-3-(piperidin-3-ylmethyl)-1H-indole, the title compound was prepared as a white solid. (Found C, 69.41; H, 6.95; N, 6.93; C$_{24}$H$_{38}$N$_2$O$_4$.0.3H$_2$O requires C, 69.65; H, 6.97; N, 6.77%); mp 197° C. (from EtOH/Et$_2$O); δ$_H$ (360 MHz; DMSO-d$_6$) 1.11–1.16 (4H, m, aliphatics), 1.18–1.41 (1H, m, aliphatic), 1.41–1.56 (2H, m, aliphatics), 1.58–1.70 (2H, m, aliphatics), 2.94–3.07 (1H, m, aliphatic), 3.18–3.38 (5H, m, aliphatics), 3.42–3.54 (1H, m, aliphatic), 7.05 (1H, t, J 7.9 and 7.1, indole H5), 7.13 (1H, t, J 7.2 and 7.1, indole H6), 7.37–7.44 (2H, m, aromatics), 7.53 (2H, t, J 7.8 and 7.4, aromatics), 7.60–7.70 (3H, m, aromatics, 11.37 (1H, br s, NH); m/z (ES$^+$) 319 (M$^+$+H, 100%).

EXAMPLE 22

3-[1-(2-Methoxyethyl)piperidin-2-ylmethyl]-2-phenyl-1H-indole hydrogen oxalate By substantially following the procedures of Example 11.C, utilising 2-phenyl-3-(piperidin-2-ylmethyl)-1H-indole in place of 2-phenyl-3-(piperidin-3-ylmethyl)-1H-indole, the title compound was prepared as a white solid. (Found C, 67.91; H, 6.91; N, 6.28; C$_{25}$H$_{30}$N$_2$O$_5$.0.2H$_2$O requires C, 67.92; H, 6.93; N, 6.34%); mp 185° C. (from EtOH/Et$_2$O); δ$_H$ (360 MHz; DMSO-d$_6$) 1.08–1.25 (1H, m, aliphatic), 1.26–1.40 (1H, m, aliphatic), 1.40–1.54 (2H, m, aliphatics), 1.60–1.70 (2H, m, aliphatics), 3.01–3.11 (1H, m, aliphatic), 3.17–3.27 (1H, m, aliphatic), 3.30 (3H, s, CH$_3$), 3.33–3.58 (5H, m, aliphatics), 3.67 (2H, t, J 4.7, aliphatics), 7.04 (1H, t, J 7.7 and 7.1, indole 1H5), 7.13 (1H, t, J 7.7 and 7.3, indole H6), 7.37–7.44 (2H, m, aromatics), 7.53 (1H, t, J 7.7 and 7.5, aromatic), 7.65–7.68 (3H, m, aromatics), 11.36 (1H, br s, NH); m/z (ES$^+$) 349 (M$^+$+H, 100%).

EXAMPLE 23

3-(1-Benzylpiperidin-2-ylmethyl)-2-phenyl-1H-indole hydrogen oxalate

By substantially following the procedures of Example 11.C, utilising 2-phenyl-3-(piperidin-2-ylmethyl)-1H-indole in place of 2-phenyl-3-(piperidin-3-ylmethyl)-1H-indole, the title compound was prepared as a white solid. (Found C, 73.40; H, 6.39; N, 5.85; C$_{29}$H$_{30}$N$_2$O$_4$ requires C, 73.46; H, 6.46; N, 5.91%); mp 235° C. (from EtOH/Et$_2$O); δ$_H$ (360 MHz; DMSO-d$_6$) 1.07–1.22 (1H, m, aliphatic), 1.29–1.46 (2H, m, aliphatics), 1.48–1.68 (3H, m, aliphatics), 2.80–2.92 (1H, m, aliphatic), 2.98–3.10 (1H, m, aliphatic), 3.30–3.45 (2H, m, aliphatics), 3.56–3.70 (1H, m, aliphatic), 4.21 (1H, d, J 13.2, PhCH$_A$H$_B$), 4.65 (1H, d, J 13.2, PhCH$_A$), 6.98 (1H, t, J 7.6 and 7.2, indole H5), 7.11 (1H, t, J 7.6 and 7.5, indole H6), 7.36–7.55 (11H, in, aromatics), 7.65 (2H, d, J 7.3, aromatics), 11.35 (1H, br s, NH); m/z (ES$^+$) 381 (M$^+$+H, 100%).

EXAMPLE 24

3-[1-(2-Phenylethyl)piperidin-2-ylmethyl]-2-phenyl-1H-indole hydrogen oxalate By substantially following the procedures of Example 11.C, utilising 2-phenyl-3-(piperidin-2-ylmethyl)-1H-indole in place of 2-phenyl-3-(piperidin-3-ylmethyl)-1H-indole, the title compound was prepared as a white solid. (Found C, 74.39; H, 6.33; N, 5.71; $C_{30}H_{32}N_2O_4$ requires C, 74.36; H, 6.66; N, 5.78%); mp 232° C. (from $EtOH/Et_2O$); $\delta_H$ (360 MHz; DMSO-$d_6$) 1.14–1.30 (1H, m, aliphatic), 1.33–1.62 (3H, m, aliphatics), 1.62–1.76 (2H, m, aliphatics), 2.80–3.02 (2H, in, aliphatics), 3.06–3.20 (1H, m, aliphatic), 3.21–3.48 (5H, m, aliphatics), 3.54 (1H, d, J 13.7, indole $CH_AH_B$), 7.05 (1H, t, J 7.5 and 7.2, indole H5), 7.13 (1H, t, J 7.5 and 7.3, indole H6), 7.21 (2H, d, J 7.1, aromatics), 7.26 (1H, d, J 7.1, indole H7), 7.30–7.34 (2H, m, aromatics), 7.36–7.41 (2H, m, aromatics), 7.47 (2H, t, J 7.6 and 7.5, aromatics), 7.60–7.72 (2H, m, aromatics), 11.38 (1H, br s, NH); m/z ($ES^+$) 395 ($M^+$+H, 100%).

EXAMPLE 25

2-(3-Fluorophenyl)-6-fluoro-3-(4-methylpiperazin-2 (S)-ylmethyl)-1H-indole dihydrochloride A. 2-(3-Fluorophenyl)-6-fluoroindole 5-Fluoro-2-iodoaniline (30 g, 126 mmol) and 3-fluorophenylacetylene (20 g, 166 mmol) were dissolved in diethylamine (500 ml) and the mixture purged with nitrogen for 10 min. Tetrakis(triphenylphosphine)palladium (2 g) and copper(I) iodide (0.4 g) were added and the mixture stirred at room temperature for 15 h. The solvent was removed in vacuo and the residue partitioned between diethyl ether (500 ml) and water (500 ml), the organic layer was separated and washed with water (2×500 ml), saturated sodium chloride (200 ml), dried over $MgSO_4$, filtered through a short plug of Florisil and evaporated in vacuo. The solid was dissolved in anhydrous DMF (500 ml), copper(I) iodide (12 g, 63 mmol) and calcium carbonate (12.6 g, 126 mmol) added and the mixture heated at 120° C. under an atmosphere of nitrogen for 48 h. The mixture was filtered through hyflo and the filtrate evaporated in vacuo. The residue was partitioned between ethyl acetate (500 ml) and water (500 ml), the organic layer was separated and washed with water (2×500 ml) and saturated sodium chloride (100 ml), dried over $MgSO_4$ and evaporated in vacuo. The residue was triturated with a mixture of diethyl ether and hexane, the solid filtered and dried in vacuo to afford 25 g (109 mmol; 87%) of 2-(3-fluorophenyl)-6-fluoroindole as a brown solid. $\delta_H$ (360 MHz; $CDCl_3$) 6.78 (1H, d, J 1.8, indole H3), 6.88 (1H, m, aromatic), 6.99 (1H, m, aromatic), 7.05 (1H, dd, J 9.5 and 2.2, aromatic), 7.29 (1H, dd, J 8.6 and 1.0, aromatic), 7.36 (2H, m, aromatics), 7.51 (1H, dd, J 8.6 and 5.3, indole H4), 8.37 (1H, br s, NH).

B. 2(R)-[6-Fluoro-2-(3-fluorophenyl)-1H-indol-3-ylcarbonyl]piperazine-1,4-dicarboxylic acid dibenzyl ester and 3-[6-fluoro-2-(3-fluorophenyl)-1H-indol-3-ylcarbonyl]-2(R)-piperazine-1-carboxylic acid benzyl ester A solution of 4.34 g (10.9 mmol) of di-N-benzyloxycarbonyl-piperazine-2(R)-carboxylic acid in anhydrous dichloromethane (100 ml) under an atmosphere of nitrogen was treated with oxalyl chloride (1.42 ml, 16.4 mmol) followed by 2 drops of N,N-dimethylformamide. The reaction mixture was stirred at room temperature for 60 min at which time the dichloromethane was evaporated in vacuo. The residue was dissolved in anhydrous toluene (25 ml) and the resulting solution evaporated in vacuo. The residue was dissolved in anhydrous benzene (50 ml) to give Solution A.

A solution of 5.0 g (21.8 mmol) of 2-(3-fluorophenyl)-6-fluoroindole in anhydrous benzene (50 ml) under an atmosphere of nitrogen was added using a cannula to a solution of methylmagnesium bromide (7.3 ml of a 3M solution in diethyl ether, 21.8 mmol) and the resulting mixture stirred at room temperature for 15 min to give Solution B.

Solution A was added in one portion to rapidly stirred solution B and the resulting mixture stirred at room temperature for 30 min. The reaction was quenched by the addition of saturated ammonium chloride solution (100 ml). The organic layer was separated, dried over $MgSO_4$ and evaporated in vacuo. The residue was purified by flash chromatography ($SiO_2$; 20% EtOAc in hexanes then 40% EtOAc in hexanes) to afford 2.4 g (3.7 mmol; 36%) of 2(R)-[6-fluoro-2-(3-fluorophenyl)-1H-indol-3-ylcarbonyl] piperazine-1,4-dicarboxylic acid dibenzyl ester as a yellow foam. $\delta_H$ (360 MHz; $CDCl_3$) 2.76–3.18 (2H, aliphatics), 3.52–3.78 (1H, aliphatic), 3.82–3.92 (1H, aliphatic), 3.94–4.04 (1H, aliphatic), 4.20–4.50 (1H, aliphatic), 4.76–5.20 (5H, aliphatics), 6.70–7.40 (18H, aromatics) 7.93 and 8.10 (1H, indole H4), 8.65 and 8.78 and 9.31 and 9.45 (1H, br s, NH); m/z ($ES^+$) 610 ($M^+$+H, 15%). Eluent changed to 3% $CH_3OH$ in $CH_2Cl_2$+0.5% $NH_3$ to afford 2.3 g (4.8 mmol; 44%) of 3-[6-fluoro-2-(3-fluorophenyl)-1H-indol-3-ylcarbonyl]-2(R)-piperazine-1-carboxylic acid benzyl ester as a yellow foam. $\delta_H$ (360 MHz; $CDCl_3$) 2.42 (1H, aliphatic), 2.68–2.90 (2H, aliphatics), 2.98 (1H, br d, J 13.0, aliphatic), 3.69 (1H, dd, J 10.2 and 3.4, aliphatic), 3.80–3.90 (1H, aliphatic), 4.00–4.16 (1H, aliphatic), 5.00–5.10 (2H, m, $PhCH_2$), 6.94–7.06 (2H, m, aromatics), 7.10–7.18 (1H, m, aromatic), 7.20–7.38 (8H, m, aromatics), 8.11 (1H, dd, J 9.0 and 5.3, indole H4), 8.83 and 9.01 (1H, br s, NH); m/z ($ES^+$) 476 ($M^+$+H, 100%).

C. [6-Fluoro-2-(3-fluorophenyl)-1H-indol-3-yl]-(1-methylpiperazin-2(R)-yl)methanone To a solution of 3-[6-fluoro-2-(3-fluorophenyl)-1H-indol-3-ylcarbonyl]-2(R)-piperazine-1-carboxylic acid benzyl ester (1.3 g, 2.7 mmol), glacial acetic acid (0.35 ml, 5.9 mmol) and sodium cyanoborohydride (255 mg, 4.1 mmol) in methanol (20 ml) was added a solution of formaldehyde (0.225 ml of a 37% w/v solution, 3.2 mmol) in methanol (5 ml), and the resulting mixture was stirred at room temperature for 2 h. To this mixture was added saturated sodium hydrogen carbonate solution (100 ml) and the mixture extracted with dichloromethane (2×50 ml); the combined organic layers were dried over $MgSO_4$ and evaporated in vacuo. The residue was dissolved in methanol (50 ml) and 1,4-cyclohexadiene (0.77 ml, 8.1 mmol) added. The flask was flushed with nitrogen and 200 mg of 10% palladium on carbon added, and the resulting mixture was heated at reflux for 18 h. The cooled reaction mixture was filtered and the filtrate evaporated in vacuo to afford [6-fluoro-2-(3-fluorophenyl)-1H-indol-3-yl]-(1-methylpiperazin-2(R)-yl) methanone (330 mg, 0.9 mmol; 33%) as a yellow foam. $\delta_H$ (360 MHz; $CDCl_3$) 1.75–1.82 (1H, m, aliphatic), 2.05 (3H, s, $CH_3$), 2.54 (1H, dd, J 12.7 and 9.0, aliphatic), 2.61–2.70 (3H, m, aliphatics), 2.76 (1H, dd, J 12.7 and 3.0, aliphatics), 3.00 (1H, dd, J 9.0 and 3.1, aliphatic), 6.82 (1H, m, aromatic), 6.97 (1H, dd, J 9.2 and 2.3, aromatic), 7.07 (1H, m, aromatic), 7.14 (1H, m, aromatic), 7.21 (1H, d, J 7.7, aromatic), 7.30–7.36 (1H, m, aromatic), 7.98 (1H, dd, J 8.8 and 5.4, indole H4), 11.60 (1H, br s, NH).

D. 2-(3-Fluorophenyl)-6-fluoro-3-(4-methylpiperazin-2(S)-ylmethyl)-1H-indole ddihydrochloride To a solution of 320 mg (0.9 mmol) of [6-fluoro-2-(3-fluorophenyl)-1H-indol-3-yl]-(1-methylpiperazin-2(R)-yl) methanone in anhydrous tetrahydrofuran (25 ml) under an atmosphere of nitrogen was added cautiously over 5 min a solution of lithium aluminium hydride (6.25 ml of a 1M solution in tetrahydrofuran, 6.25 mmol) at 0° C. The mixture was heated under reflux for 3 hr, after which it was cooled and quenched by careful addition of water (0.25 ml), 4N NaOH (0.25 ml), and water (0.75 ml). The mixture was stirred for 10 min then filtered through hyflo and evaporated in vacuo. The residue was purified by column chromatography ($SiO_2$; 2% MeOH in $CH_2Cl_2$+0.5% $NH_3$ then 4% MeOH in $CH_2Cl_2$+0.5% $NH_3$), and the dihydrochloride salt formed from MeOH/$Et_2O$ to afford 88 mg (0.2 mmol; 24%) of 2-(3-fluorophenyl)-6-fluoro-3-(4-methylpiperazin-2(S)-ylmethyl)-1H-indole dihydrochloride as a tan solid (Found:

C, 55.28; H, 5.67; N, 9.70; $C_{20}H_{21}F_2N_3 \cdot 1.1H_2O$ requires C, 55.33; H, 5.85; N, 9.68%); mp 228° C. (from $MeOH/Et_2O$); $\delta_H$ (360 MHz; $D_2O$) 2.61 (3H, s, $CH_3$), 2.70 (1H, br t, J 13.4 and 12.1, aliphatic), 2.76–2.86 (2H, m, aliphatics), 2.98 (1H, br d, J 12.4, aliphatic), 3.10 (1H, m, aliphatic), 3.26 (1H, br d, J 13.4, aliphatic), 3.36–3.42 (2H, m, aliphatics), 7.00 (1H, m, aromatic), 7.17–7.24 (3H, m, aromatics), 7.31 (1H, d, J 7.7, aromatic), 7.51–7.57 (2H, m, aromatics); m/z ($ES^+$) 342 ($M^+$+H, 100%).

EXAMPLE 26

2-(3-Fluorophenyl)-6-fluoro-3-(1-methylpiperazin-2(S)-ylmethyl)-1H-indole dihydrochloride To a solution of 1 g (2.1 mmol) of 3-[6-fluoro-2-(3-fluorophenyl)-1H-indol-3-ylcarbonyl]-2(R)-piperazine-1-carboxylic acid benzyl ester in anhydrous tetrahydrofuran (50 ml) under an atmosphere of nitrogen was added cautiously over 5 min a solution of lithium aluminium hydride (12.5 ml of a 1M solution in tetrahydrofuran, 12.5 mmol) at 0° C. The mixture was heated under reflux for 3 hr, after which it was cooled and quenched by careful addition of water (0.5 ml), 4N NaOH (0.5 ml), and water (1.5 ml). The mixture was stirred for 10 min then filtered through hyflo and evaporated in vacuo. The residue was purified by preparative TLC (15% MeOH in $CH_2Cl_2$+0.5% $NH_3$), and the dihydrochloride salt formed from $MeOH/Et_2O$ to afford 125 mg (0.3 mmol; 14%) of 2-(3-fluorophenyl)-6-fluoro-3-(1-methylpiperazin-2(S)-ylmethyl)-1H-indole dihydrochloride as a tan solid, mp 200° C. (from $MeOH/Et_2O$); $\delta_H$ (400 MHz; $D_2O$) 2.02–2.12 (1H, m, aliphatic), 2.36 (1H, t, J 11.4, aliphatic), 2.46 (3H, s, $CH_3$), 2.84–2.93 (1H, m, aliphatic), 3.05 (1H, br d, J 12.5, aliphatic), 3.14 (1H, br d, J 13.3, aliphatic), 3.19–3.25 (3H, m, aliphatics), 3.31–3.39 (1H, m, aliphatic), 6.99–7.05 (1H, m, aromatic), 7.20–7.27 (2H, m, aromatic), 7.38 (1H, doublet of triplets, J 10.0 and 2.2 and 1.8, aromatic), 7.44 (1H, d, J 7.8, aromatic), 7.54–7.61 (1H, m, aromatic), 7.63 (1H, dd, J 8.8 and 5.3, indole H4); m/z ($ES^+$) 342 ($M^+$+H, 100%).

What is claimed is:

1. A compound of formula I, or a salt thereof:

(I)

wherein

A and B independently represent hydrogen, halogen, cyano, nitro, trifluoromethyl, trifluoromethoxy, $C_{1-6}$ alkyl or $C_{1-6}$ alkoxy;

X and Y independently represent hydrogen, halogen, trifluoromethyl, trifluoromethoxy, $C_{1-6}$ alkyl, $C_{1-6}$ alkoxy or phenyl; and Q is selected from the structures of formula Qa to Qm:

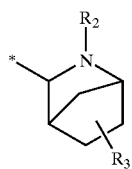

in which the asterisk denotes the point of attachment to the remainder of the molecule;

Z represents oxygen, sulphur or N—R$^1$;

R$^1$ and R$^2$ independently represent hydrogen, or C$_{1-6}$ alkyl, aryl(C$_{1-6}$)alkyl or C$_{3-7}$ heterocycloalkyl(C$_{1-6}$) alkyl, any of which groups may be optionally substituted by one or more substituents; and R$^3$ represents hydrogen, halogen, C$_{1-6}$ alkyl, hydroxy or C$_{1-6}$ alkoxy; provided that at least one of R$^1$, R$^2$ and R$^3$ is other than hydrogen.

2. A compound as claimed in claim 1 wherein Q represents a group of formula Qc.

3. A compound as claimed in claim 1 represented by formula II, and salts thereof:

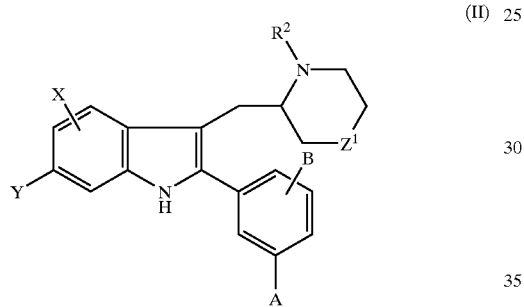

wherein

Z$^1$ represents oxygen, N—R$^1$ or CH—R$^3$.

4. A compound selected from:
3-(1-methylpiperidin-3-ylmethyl)-2-phenyl-1H-indole;
3-(1-methylpyrrolidin-3-ylmethyl)-2-phenyl-1H-indole;
3-(1-methylpyrrolidin-2(R)-ylmethyl)-2-phenyl-1H-indole;
3-(1-methylpyrrolidin-2(S)-ylmethyl)-2-phenyl-1H-indole;
2-methyl-3-(2-phenyl-1H-indol-3-ylmethyl)-2-azabicyclo[2.2.2]octane;
3-(2-methyl-2-azabicyclo[2.2.1]hept-3-ylmethyl)-2-phenyl-1H-indole;
3-(1,5-dimethyl-cis-pyrrolidin-2-ylmethyl)-2-phenyl-1H-indole;
3-(1,4-dimethylpiperazin-2(S)-ylmethyl)-2-phenyl-1H-indole;
7-chloro-3-(1,4-dimethylpiperazin-2(S)-ylmethyl)-2-phenyl-1H-indole;
3-(4-methylmorpholin-3-ylmethyl)-2-phenyl-1H-indole;
3-[1-(2-phenylethyl)piperidin-3-ylmethyl]-2-phenyl-1H-indole;
3-(1-benzylpyrrolidin-2-ylmethyl)-2-phenyl-1H-indole;
3-[1-(2-phenylethyl)pyrrolidin-2-ylmethyl]-2-phenyl-1H-indole;
2-phenyl-3-[1-(3-phenylpropyl)pyrrolidin-2(R)-ylmethyl]-1H-indole;
3-(1-benzylpyrrolidin-3-ylmethyl)-2-phenyl-1H-indole;
3-[1-(2-phenylethyl)pyrrolidin-3-ylmethyl]-2-phenyl-1H-indole;
3-(1-methylpiperidin-2(R)-ylmethyl)-2-phenyl-1H-indole;
3-(1-methylpiperidin-2(S)-ylmethyl)-2-phenyl-1H-indole;
3-(1-methylazepin-2(R)-ylmethyl)-2-phenyl-1H-indole;
3-(1-methylazepin-2(S)-ylmethyl)-2-phenyl-1H-indole;
3-(1-ethylpiperidin-2-ylmethyl)-2-phenyl-1H-indole;
3-[1-(2-methoxyethyl)piperidin-2-ylmethyl]-2-phenyl-1H-indole;
3-(1-benzylpiperidin-2-ylmethyl)-2-phenyl-1H-indole;
3-[1-(2-phenylethyl)piperidin-2-ylmethyl]-2-phenyl-1H-indole;
2-(3-fluorophenyl)-6-fluoro-3-(4-methylpiperazin-2(S)-ylmethyl)-1H-indole;
2-(3-fluorophenyl)-6-fluoro-3-(1-methylpiperazin-2(S)-ylmethyl)-1H-indole; and salts thereof.

5. A process for the preparation of a compound as claimed in claim 1, which comprises:

(A) attachment of the requisite substituent to a precursor compound of formula III:

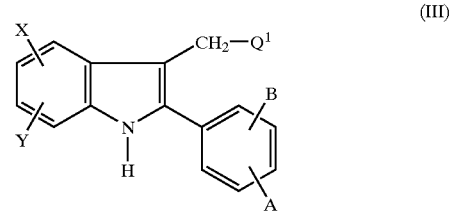

wherein A, B, X and Y are as defined in claim 1, and Q$^1$ corresponds to a moiety of formula Q as defined in claim 1 in which R$^1$ and R$^2$ independently represent hydrogen; or (B) reducing a compound of formula V:

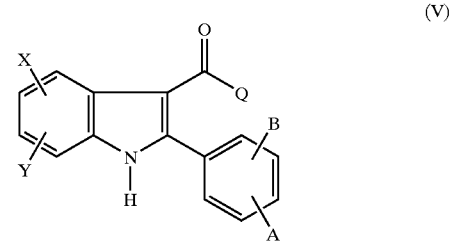

wherein A, B, X, Y and Q are as defined in claim 1; or (C) reducing a compound of formula VI:

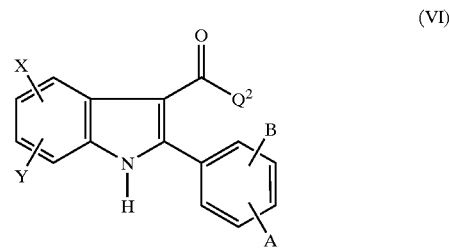

wherein A, B, X and Y are as defined in claim 1, and Q$^2$ corresponds to a moiety of formula Q as defined in claim 1 in which R$^1$ and R2 independently represent a benzyloxycarbonyl group; or (D) reacting a compound of formula X or an acid adition salt thereof with a compound of formula XI:

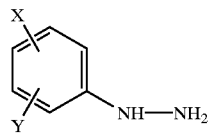 (X)

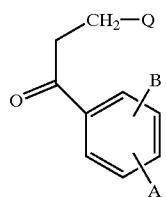 (XI)

wherein A, B, X, Y and Q are as defined in claim 1; and (E) subsequently, where required, converting a compound of formula I initially obtained into a further compound of formula I by conventional methods.

6. A pharmaceutical composition comprising a compound of formula I as defined in claim 1 or a pharmaceutically acceptable salt thereof in association with a pharmaceutically acceptable carrier.

7. A composition as claimed in claim 6 further comprising another anti-schizophrenic medicament.

8. A method for the treatment of a psychotic disorder which comprises administering to a patient in need of such treatment an effective amount of a compound of claim 1 or a pharmaceutically acceptable salt thereof.

* * * * *